(12) United States Patent
Veas et al.

(10) Patent No.: US 7,078,038 B1
(45) Date of Patent: Jul. 18, 2006

(54) GP120 MUTANTS AND BIOLOGICAL APPLICATIONS

(75) Inventors: Francisco Veas, Mauguio (FR); Martine Cerutti, Saint Christol Lez Ales (FR)

(73) Assignee: Institut de Recherche pour le Developpement (I.R.D.), Paris Cedex (FR)

( * ) Notice: Subject to any disclaimer, the term of this patent is extended or adjusted under 35 U.S.C. 154(b) by 0 days.

(21) Appl. No.: 09/856,707

(22) PCT Filed: Nov. 29, 1999

(86) PCT No.: PCT/FR99/02949

§ 371 (c)(1),
(2), (4) Date: Jun. 21, 2001

(87) PCT Pub. No.: WO00/32786

PCT Pub. Date: Jun. 8, 2000

(30) Foreign Application Priority Data

Nov. 27, 1998 (FR) .................................. 98 14997

(51) Int. Cl.
*A61K 39/21* (2006.01)
(52) U.S. Cl. .................................. 424/188.1; 424/208.1
(58) Field of Classification Search ............. 424/188.1, 424/208.1; 435/69.1
See application file for complete search history.

(56) References Cited

U.S. PATENT DOCUMENTS

| 5,792,459 A | 8/1998 | Haigwood |
| 2003/0104577 A1* | 6/2003 | Lingappa et al. .......... 435/69.3 |

OTHER PUBLICATIONS

Hansen, J. E., et al., 1996, "Prediction of the secondary structure of HIV-1 gp120.", PROTEINS: Structure, Function, and Genetics 25:1-11.*
Gross, I., et al., 1997, "In vitro assembly properties of purified bacterially expressed capsid proteins of human immunodeficiency virus.", Eur. J. Biochem. 249:592-600.*
Vlasuk, G.P., et al., 1989, "Purification and characterization of human immunodeficiency virus (HIV) core precursor (p55) expressed in *Saccharomyces cerevisiae*.", J. Biol. Chem. 264(20):12106-12112.*
Quinones-Mateu, M. E. et al.: "Molecular characterization of human imunodeficiency virus type 1 isolates from Venezuela." AIDS Research and Human Retroviruses, vol. 11, No. 5, 1995, pp. 605-616.
Misse D. et al. "Dissociation of the CD4 and CXCR4 binding properties of human inununodeficiency virus type 1 gp120 by deletion of the first putative alpha-helical conserved structure" Journal of Virology, vol. 72, No. 9, Sep. 1998, pp. 7280-7288.
Willey, R.L. et al.: "Amino acid substitutions In the human inununodeficiency virus type 1 gp120 V3 loop that change viral tropism also alter physical and functional properties of the virion envelope." Journal of Virology, vol. 68, No. 7, Jul. 1994, pp. 4409-4419.
Thali, M. et al.: "Discontinuous, conserved neutralization epitopes overlapping the CD4-binding region of human inmiunodeficiency virus type 1 gp120 envelope glycoprotein." Journal of Virology, vol. 66, No. 9, Sep. 1992, pp. 5635-5641.
Cordonnier, A. et al.: "Single amino-acid changes in HIV envelope affect viral tropism and receptor binding." NATURE, vol. 340, Aug. 1989, pp. 571-574.
Korber, B.T.M. et al.: "Genetic differences between blood- and brain-derived viral sequences from huamn immunodeficiency virus type 1-infected patients: evidence of conserved elements in the V3 region of the envelope protein of brain-derived sequences." Journal of Virology, vol. 68, No. 11, Nov. 1994, pp. 7467-7481.
Lund, O. et al.: "Inhibition of HIV type 1 infectivity by coexpression of a wild-type and a defective glycoprotein 120." AIDS Research and Human Retroviruses, vol. 14, No. 16, Nov. 1998, pp. 1445-1450.
Kwong, P. D. et al.: "Structure of an HIV GP120 envelope glycoprotein in complex with the CD4 receptor and a neutralizing human antibody." NATURE, vol. 393, Jun. 1998, pp. 648-659.

* cited by examiner

*Primary Examiner*—Jeffrey S. Parkin
(74) *Attorney, Agent, or Firm*—Nixon & Vanderhye P.C.

(57) ABSTRACT

An isolated and purified human immunodeficiency virus type 1 (HIV-1) mutant gp120 envelope glycoprotein containing an amino acid mutation in position 112 which contains replacement of W with S, I, or F, wherein the numbering scheme is based upon the molecular clone HxBc2.

3 Claims, 5 Drawing Sheets

GP120 MUTANTS AND BIOLOGICAL APPLICATIONS

Figure 1:
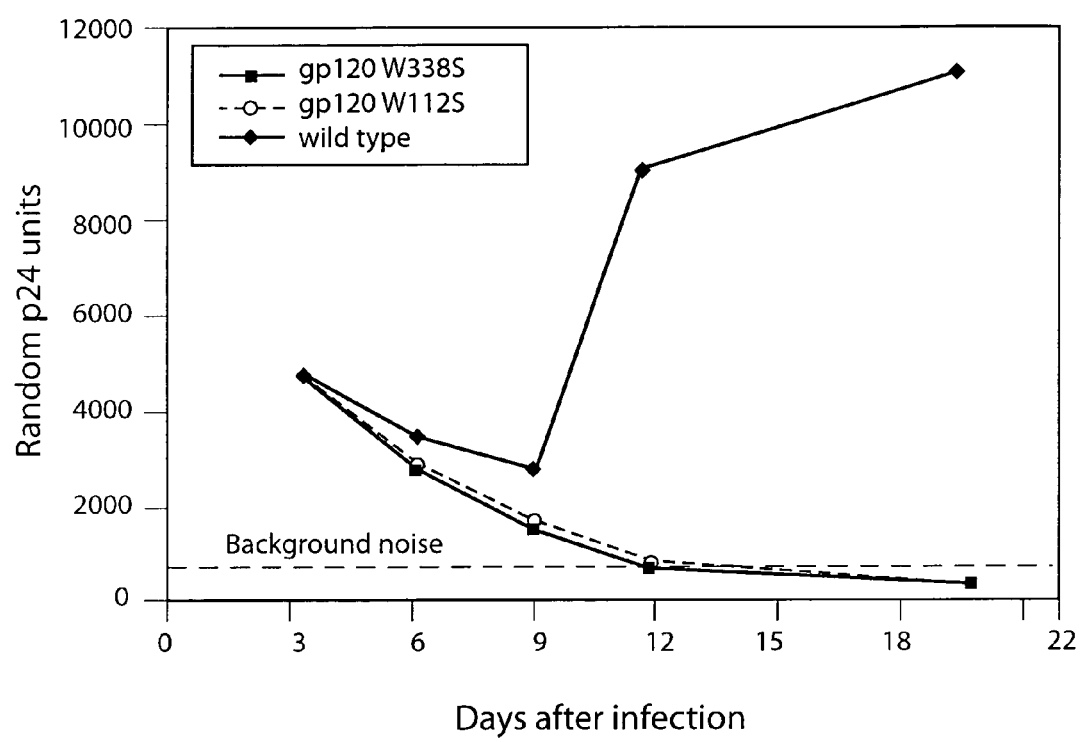

The present application is a 371 U.S. national phase of International application PCT/FR99/02949, filed 29 Nov. 1999.

The present invention relates to qp120 mutants and their applications

It is known that interactions between the CD4 of target cells and HIV gp120 involve conserved gp120 regions, in particular a tryptophan (W) at position 427 according to the amino acid numbering described by Kwong et al (ref. 1 in the bibliography given at the end of this description).

In the article by Missé et al [2], some of whose co-authors are co-inventors in the present application, it was shown that a stable structure, a so-called conserved gp120 structure, contained in the C1 zone, namely the amphipathic α1 helix, is involved in interactions with the CD4 receptor. In addition, a gp120 construct with no α1 helix showed that an interaction still remains possible with the target cell, in particular with the CXCR4 receptor, the chimiokine receptor on the lymphocytes.

By inducing specific point mutations in the conserved structures of gp120, the α2 helix in particular, the inventors have identified the essential role played by these structures in the interactions with target cells, whether directly or indirectly. The trans-conformation of these structures subsequent to a given mutation made it possible, as illustrated in the examples to unmask regions that are normally hidden and which are involved in these interactions, and therefore to make molecules available that are able to act as vaccine targets.

The invention therefore concerns mutants of gp120, characterized in that they contain at least one mutation in a region rich in aromatic amino acids, and especially of the α2 helix of gp120, and optionally the α1 helix.

The mutants of the invention contain at least one mutation, this mutation being located in the gp120 region corresponding to the interaction cavity with CD4.

The invention particularly concerns the gp120 mutants in W at position 112 is replaced by a non-aromatic amino acid such as a serine S.

Said mutation induces a total absence of cell fusion. Cell fusion tests, which are reported below in the example section, therefore show that the W112S substitution annihilates the formation of syncytia between HeLa-Tat cells (expressing a gp160 containing this mutation) and HeLa P4 cells Moreover, a virus containing this same mutation is unable to infect human lymphocytes. Substitution of this same W (bicyclic aromatic residue) by a (monocyclic) aromatic residue reduces but does not suppress these functions.

In addition, in said mutants, the recognition by antibodies specific to the CD4 binding site, as defined by Cordonnier et al [3], is greatly reduced.

These results therefore show the capital role played by the conserved 60 1 helical structure in fixation to CD4.

In addition to mutation at position 112, such mutants may also comprise a mutation of F at position 383 to alanine, and optionally, of tryptophan at position 427 replaced by a glycine and/or of tryptophan at position 479 replaced by a non-aromatic amino acid, such as serine or isoleucine.

The crystallographic data published in [1] led to visualizing firstly the position of the alpha 1 helix of gp120 in this three-dimensional structure, and secondly to visualizing tryptophan residues.

These data confirmed the results of the biological experiments mentioned above.

In particular, W 112 is located in the hydrophobic pocket described as the gp120-CD4 interaction pocket; this pocket is formed of a "cluster" of aromatic residues which apparently interacts with another aromatic residue, the F43 of CD4. Also, it arises from this study that the tryptophan residues hold a strategic position in this pocket. Therefore any mutation of one of them would destabilize this "cavity" and would prevent any binding with the F43 of CD4.

Other mutants according to the invention optionally also contain, in addition to the above-mentioned mutations in the α1 helical structure, at least one mutation which is positioned in the gp120 region corresponding to the α2 helical structure, downstream from the V3 loop of gp120.

The invention particularly concerns the mutant in which W at position 338 is replaced by a serine.

This unique mutation is able to induce a total absence of cell fusion when CXCR4" and cells expressing the W338S muted gp120 are placed in the presence of target CD4" cells.

The virus complemented by an enveloped containing the W3385 mutation at gp120 is no longer able to infect the cells (see FIG. 1).

As noted above, since W forms part of the conserved α2 structure, this amino acid is therefore found in the second pocket containing aromatic residues and hydrophobic residues.

This mutation therefore suggests that this structure is involved in the interaction with the co-receptors, CXCR4 for example, having regard to biological results.

The mutants according to the invention, by allowing examination of the role played by conserved structures, provide a new method of approaching interactions between infectious agents-target cells. By gaining a better understanding of the functionality of the different conserved structures involved in pathogen agent-target cell interactions, it is possible to devise therapeutic or immunizing molecules against. HIV.

Taking advantage of the identification of these interaction pockets, the invention targets compounds able to mimic CD4 and therefore having inhibitor properties against gp120.

It also targets peptides mimicking the extracellular loops of co-receptors, able to lodge themselves in said hydrophobic pockets.

The invention also concerns peptides able to mimic the above-mentioned gp120 constant regions and likely to form candidates as vaccines. The invention therefore provides models for the preparation of such candidates.

In addition, by conducting mutations on the first cavity, it is possible to induce gp120 transformations allowing better exposure of the second cavity, and hence of gp120 as antigen. In advantageous manner, an adapted immune response is therefore obtained against these constant regions that are visually hidden.

Through said transformations, it is also possible to induce dissociations between gp120 and gp41. As shown in the examples given below, no fusion is observed when viruses are used which are complemented with a gp160 containing a mutation at gp120, whereas the glycoprotein responsible for the fusion is gp41. Mutation on gp120 therefore forms a target to prevent fusion of the virus. In this manner key epitopes are made available to prevent infection by HIV.

Figure 2A:
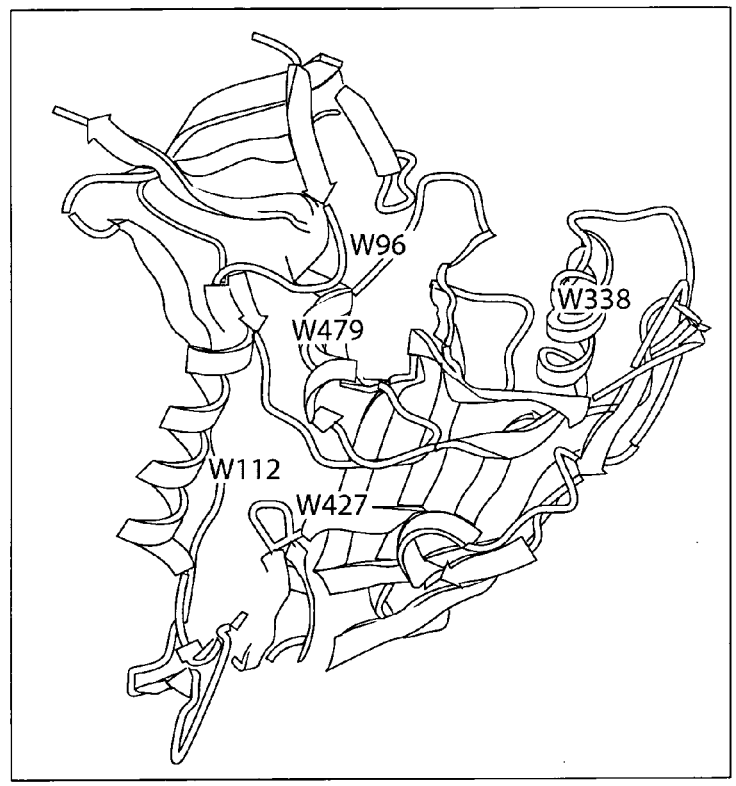
Figure 2B:
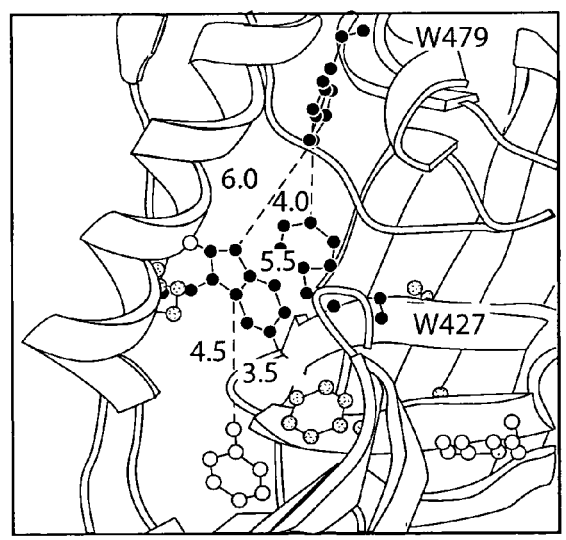

Other characteristics and advantages of the invention are given in the following examples, in which reference is made to FIGS. 1 to 8 which respectively show:

FIG. 1: the results of infectivity tests of HIV-1 pseudovirus complemented with an envelope containing mutations according to the invention at gp120, FIG. 2: the crystalline structure of gp120,

```
96W/S    5'AAC GTG ACA GAA AAT TTT AAC ATG AGT AAA AAT G3'   (SEQ ID NO:1)

112W/S   5'GAT ATA ATC AGT TTA TCT GAT CAA AGC3'             (SEQ ID NO:2)

96W/1    5'AAC GTG ACA GAA AAT TTT AAC ATG ATC AAA AAT G3'   (SEQ ID NO:3)

112W/1   5'GAT ATA ATC AGT TTA ATC GAT CAA AGC3'             (SEQ ID NO:4)

96W      5'AAC GTG ACA GAA AAT TTT AAC ATG TGG AAA AAT G3'   (SEQ ID NO:5)

112W     5'GAT ATA ATC AGT TTA TGG GAT CAA AGC3'             (SEQ ID NO:6)
```

Figure 3:
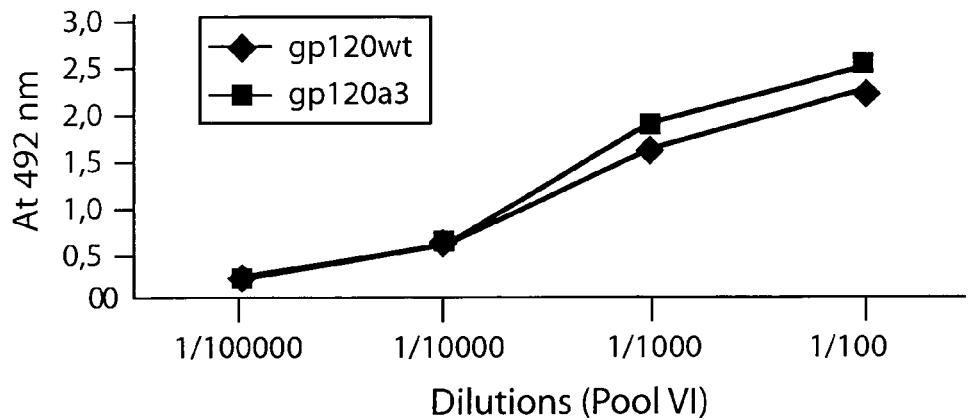
Figure 4:
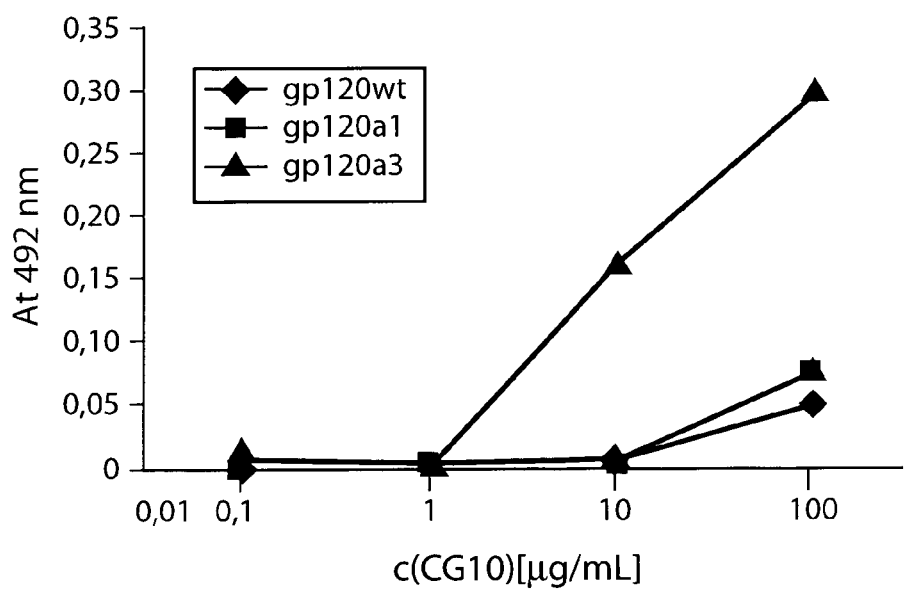

FIG. 3: the results of biological activity tests of rgp120, with a rabbit anti-gp120 polyclonal antibody, FIG. 4: the reactivity of rgp120 with AcM CG10.

Figure 5:
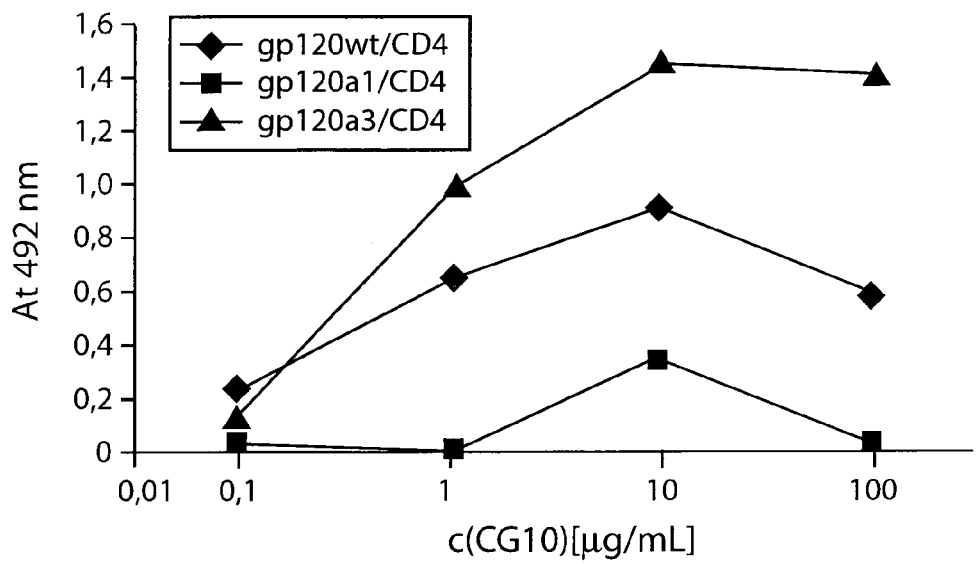
Figure 6:
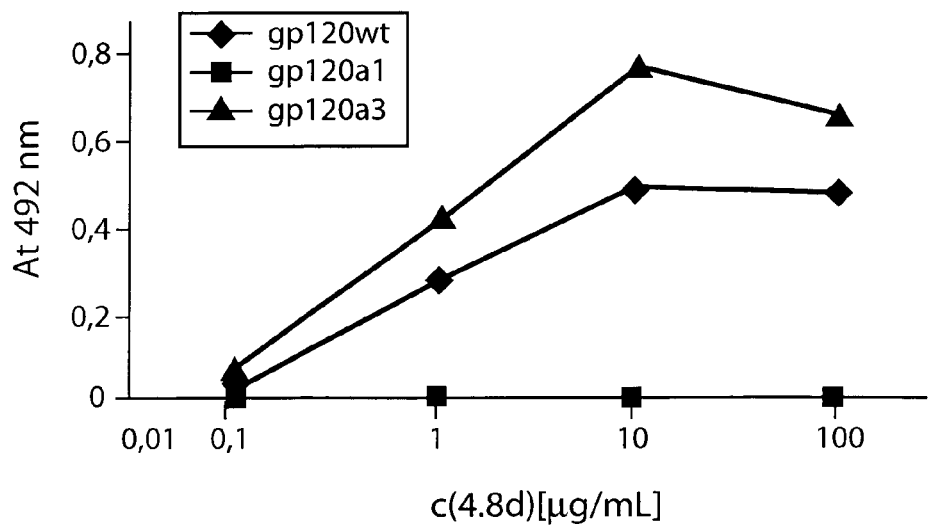
Figure 7:
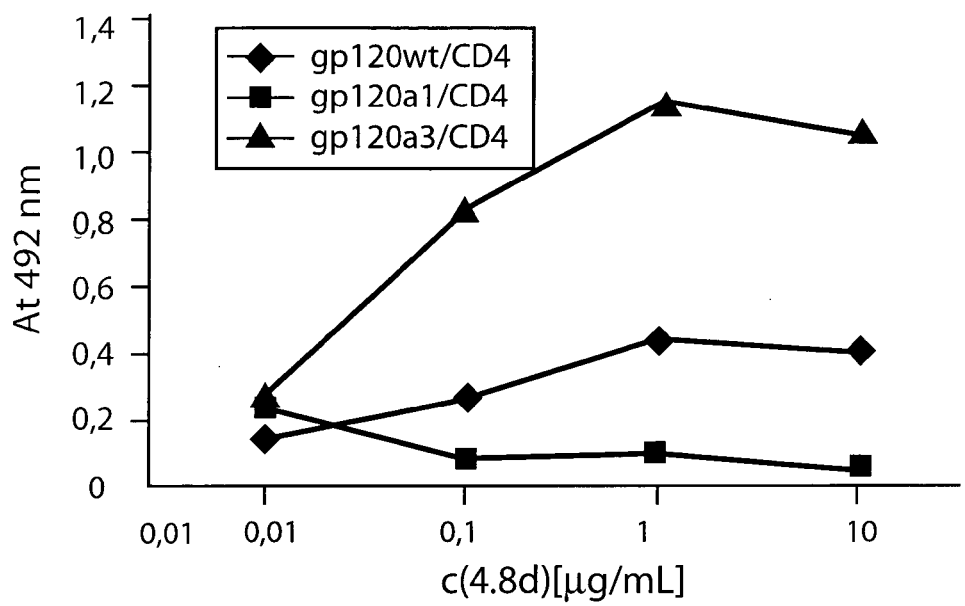

FIG. 5: the reactivity of rgp120 complexed to CD4 with AcM CG10,

FIG. 6: the reactivity of rgp120 with AcM 4.8d,

FIG. 7: the reactivity of rgp120 complexed to CD4 with AcM 4.8d, and

Figure 8:
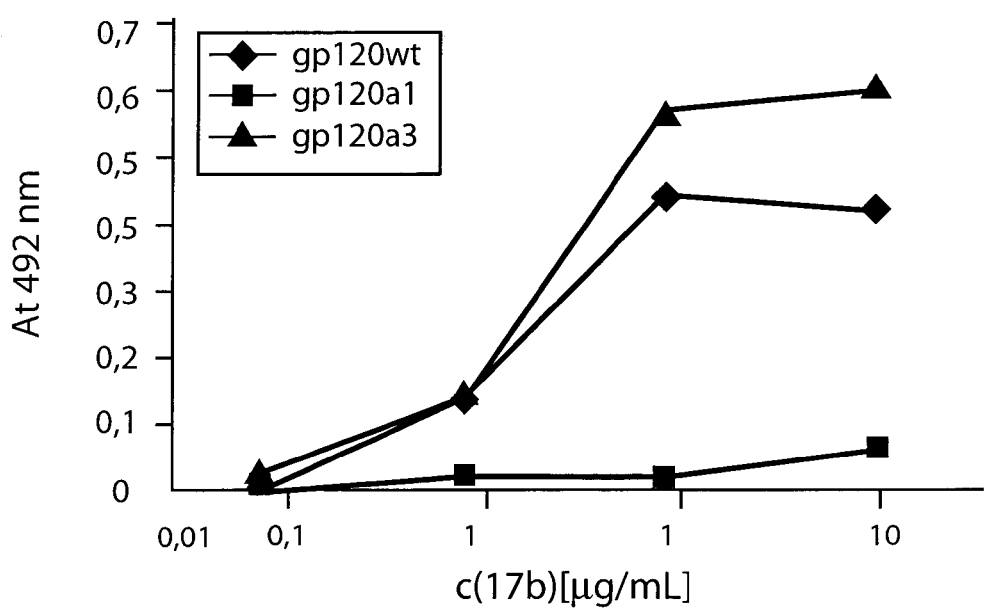

FIG. 8 : the reactivity of rgp120 with AcM 17b.

EXAMPLE

Production and Study of gp120 Mutants

These gp120 mutants were tested in several biological systems:
(i) cell fusion (envelopes muted on the cell surface), (ii) viral infections (pseudo-viruses complemented with muted gp120's), (iii) analysis of the topology of these muted gp120's made by different monoclonal antibodies recognizing different gp120 epitopes in the "CD4 binding sites", and (iv) gp120 analysis using crystallographic data.

These experiments were conducted using the following material and methods:

Plasmids, antibodies and pseudoviruses

The pHXB2ENV plasmid (code for the qp160-envelope of HIV-IIIS), the pCMV-rev plasmid (code for the Rev protein controlled by the CMV promoter), and the 902 monoclonal antibody (directed against the V3 loop of gp120) were obtained from NIH AIDS Research and Reference Reagent Program (USA). The pNL4-3env-GFP pseudovirus was supplied by Dana-Farber Cancer Institute, Boston, USA. This plasmid contains the genome of HIV-1 NL4-3 deleted from the Env gene, and a substitution of the Nef gene by the gene encoding the GFP protein (Green Fluorescent Protein).

Directed mutagenesis in the alpha 1 helix of gp120

For the purpose of examining the W residues present in the alpha 1 helical structure of gp120, the NdeI-HindII region of the gene coding for gp120 was reconstructed. For this purpose, an oligonucleotide was used in which two restriction sites were inserted (HpaI and HindIII) surrounding the α1 helix [2]. The α1 helix of gp120 has two tryptophan residues (W96 and W112) [4]. The HpaI and Hind III sites were used to exchange a wild HPaI-Hind III fragment for a fragment of muted HpaI-Hind III for each construct. Mutations were made either simultaneously on both Ws or on a single tryptophan. Directed mutagenesis was conducted using the overlapping oligonucleotide method between the HpaI and Hind III sites of the pBs plasmid. Table I below only gives those oligonucleotides which contain the desired mutation.

Cell-cell fusion

The expression vectors containing the different gp160 envelopes (pHXB2ENV, 500 ng) were co-transfected with 500 ng of pCMV-rec in HeLa-Tat cells. The transfection method used was lipofection (lipofectamine, GIBCO) as described in [2].

pCMV-re is indispensable for activating the expression of the ENV gene present in the pHXB2 ENV plasmid. The transfected cells were then placed in co-culture with the HeLAP4 cells (CD4-LTR Lacz) as described in [2].

Expression of muted gp120's on the cell surface

The transfection technique used was the same as the one used for cell-cell fusion.

Twenty-four hours before co-transfection the HeLa-Tat cells were placed in wells 3.5 cm in diameter with coverglasses (12 mm in diameter). The cells were incubated 48 hours after co-transfection with ACm 902 (directed against the V3 loop of gp120) at a concentration or 10 µg/ml. This incubation was conducted in the presence of 0.1% sodium azide ($NaN_3$) and in PBS buffer. After 2 washings in PBS, 0.3% BSA/0.1 $NaN_3$, the cells were then incubated with a mouse anti-igG antibody labelled with Texas-red (molecular probes). After 3 extensive washings, the cells were fixed for 2 minutes with an ethanol-acetone mixture (1:2). After mounting the coverglasses on slides with Mowiol, the cells were observed under confocal microscopy.

ELFA Assay of p24 (Enzyme Linked Fluorescent Assay)

The assay of p24 was conducted with the automated VIDAS HIV DUO system (BioMérieux). This test is based on simultaneous detection of p24 antigenaemia and anti-HIV-1 and anti-HIV-2 antibodies. The principle of the assay associates two immuno-enzymatic reactions with fluorescence detection. This test is provided with a disposable cone which serves both as solid phase and as pipetting system. In the lower part of the cone, three synthesis peptides are fixed (gp41, gp36 and a specific type 0 peptide) conjugated with mouse anti-human IqG Acms labelled with alkaline phosphatase. In the upper part of the cone anti-p24 Acms are fixed. During the assay a rabbit anti-p24 biotinylated antibody (conjugated with alkaline streptavidin-phosphatase) is added at the same time as the sample. The substrate, 4-methyl-ombelliferyl-phosphate, is used to measure fluorescence which is proportional to the quantity of anti-HIV Ac and/or Ag p24 present in the sample. The reaction occurs in 90 minutes and fluorescence is read with the specific reader for the VIDAS assay (wavelength 450 nm).

Infections of human lymphocytes with muted pseudo viruses obtained by complementation.

293 cells were co-transfected with 10 µg pNL4-3 GFP pseudovirus, 2 µg of pHXB2 ENV plasmid (which may or may not contain the different mutations in SU gp120) and 1.5 µg of pCMV-rev plasmid. The calcium phosphate transfection method was used. Forty-eight hours after transfection, the cell supernatants were sampled, filtered and stored at −80° C. until use. Measurement of p24 was then made on these different supernatants. Human lymphocytes previously stimulated for 3 days with 10 µg/ml PHA (Phytohemaglutinine), 50 U of IL-2 in a culture of RPMI 1640–10% FCS (Foetal Calf Serum), were incubated with the different supernatants of transfected 293 cells (containing an identical p24 concentration).

The infecting capacities of the different supernatants were visualized under fluorescence microscopy (expression of GFP protein in the lymphocytes and determined by assay of the p24 (periodic follow-up every 3 days) in the culture supernatants of infected lymphocytes.

Structural Analyses

The structure of the complex formed by the core of gp120, the first two domains of CD4 and the Fab fragment of the neutralizing antibody 17b were recently determined by X-ray crystallography [1]. This structure was filed in the protein data base (pdb) under the access code "Igcl". The structural coordinates of this complex were analysed with Insight 1 software (MSI for Molecular Simulations) on Silicon Grafic $O_2$. Visualization and modelling of the domains of gp120 and CD4 were made using the Discover program (MSI) in an Insight II environment.

Results

Fusiogenic capacities of gp160 envelopes

In order to asses the fusiogenic capacities of the different gp160 envelopes expressed on the surface of the transfected HeLa-Tat cells, these cells were placed in co-culture with HeLa P4 cells (CD4 LTR LacZ).

The results obtained are given in Table 2 below:

TABLE 2

| Mutations in gp 120 | Percentage of fusion foci |
|---|---|
| Wild type | 100% (approx. 1500 fusion foci/well) |
| 96 W/S and 112 W/S | 0% |
| 96 W/I and 112 W/I | 0% |
| 96 W/F and 112 W/F | 60% |
| 96 W/F | 100% |
| 112 W/F | 60% |
| 96 W/S | Non-determined |
| 112 W/S | 0% |
| 427 W/S | 0% |
| 338 W/S | 0% |
| Control | 0% |

It is found on examining these results that simultaneous mutations on both tryptophan residues of the alpha 1 helix (w96 and W112) to serine or to isoleucine make the gp160 envelope incapable of inducing syncytia between the cells. The same phenomenon is observed with the gp160 envelope containing the point mutation 112 W/S and/or 338 W/S. On the other hand, the substitution of a tryptophan residue (W) by an aromatic phenylalanine residue (F), having a close hydrophobicity index, reduces the fusiogenic capacities of the muted envelopes by about 50%. It is noticed that, irrespective of the construct, this phenomenon is observed solely when the W112 residue and/or the W338 residue is (are) involved, which denotes the biological importance of this or these residue(s) compared with the W96 group (within the scope of these experiments). All these results were compared with those obtained with the wild gp160 envelope (in which approximately 1500 fusion foci were observed). The negative control was the placing in co-culture of non-transfected HeLa-Tat cells with HeLA P4 coils (no fusion foci were observed).

These results indicate that the W112 residue and/or the W338 residue is or are involved in gp120-target cell interactions, which precede the phenomenon of cell fusion.

Expression of gp120 proteins on the cell surface.

gp120 was detected by Acm 902, directed against the V3 loop of gp120. The latter was then developed with a mouse anti-IgG coupled with Texas Red. It is found that both the wild gp120 and the 112W/S gp120 are expressed on the surface of the cells. The incubation of the 902 antibody with non-transfected HeLa-Tat cells gives no signal.

Infective capacities of complemented pseudo-viruses.

FIG. 1 shows the changes in the p24 level in the supernatants of lymphocytes (previously activated with 10 μg/ml PHA and 50 U/ml of IL2) placed in contact. with:

- the pseudovirus complimented with wild type gp120 (tracing with ●),
- the pseudovirus complemented with muted gp120 (112W/S gp120) (tracing with ○),
- the pseudovirus complemented with muted gp120 (gp120 338W/S) (tracing with ■)

In the first case, the p24 level is firstly reduced and then increases considerably (on and after the $10^{th}$ day after infection), which proves the presence of a de novo synthesized p24, the product of a viral infection.

In the second case, the p24 level reduces gradually to disappear completely on the $20^{th}$ day (after contacting). No cell infection therefore occurred due to the 112W/S mutation in gp120. This fact was confirmed by the absence of expression of the GFP protein in the cells incubated with the muted virus 112 W/S and/or 338 W/S (visualization under fluorescence microscopy).

The lack of cell infection observed in this latter case may be explained by the absence of any syncytia formation previously visualizes with cells expressing gp120 W/S and/or gp120 338 W/S on their surface.

Three-dimensional analysis and structural locating of the conducted mutations

The crystallographic structure of the gps120-CD4-17b Fab complex has recently been determined [3] with a resolution of 2.5A (FIG. 2)

The coordinates of this structure were analysed using Insight II software, with which it was possible to place the amino acids in a three-dimensional context with much higher resolution than with the predictive models which prompted our approach.

Analysis of the crystallographic structure of the gp120-CD4 complex shows a reduced number of residues forming the interface between the two proteins. The majority interaction between gp120 and CD4 is located at a hydrophobic pocket, involving the W427 amino acid of gp120 and the F43 residue of CD4 (Wyatt et Coll. 1998).

In addition, as shown in FIG. 3, W112 is strategically located in this cavity rich in aromatic residues and interacts directly with the F43 of CD4. F43 apparently places itself in the middle of this pocket and would seem to interact directly with W112. The interaction of W112 with F43 and W427 apparently makes it possible to stabilize the entire hydrophobic pocket. It is to be noted that W112 and W427 are located at a distance of 5 Å or less from each other, which indicates that these two tryptophan residues are likely to interact strongly.

This interaction could occur through a stacking effect of the aromatic cores between these two residues or by dipoledipole binding. Also, these distances may in fact prove to be much shorter taking into account the dynamic aspect of in vivo molecular interactions.

Crystalline analysis also led to discovering that W338 of the α2 helix is likely to play a major role in the stability of the second cavity (out of a total of 2 cavities included inside gp120), formed of the hydrophobic and aromatic residues. Under these conditions, this cavity may be considered to be capital in the interactions with gp120 and the co-receptors, CXCR4 for example.

Experiments identifying the involvement of W386S mutation on the HIV-1 gp120 of the HXB2 clone of HIV-IIIB in terms of its structure and function.

FUNCTION: fusiogenic capacities gp120 expressed on the surface of transfected cells and infective capacities of viruses having envelopes with muted or non-muted gp120s No observation is made
- of any fusion foci in the fusion tests between HeLa-P4 cells (CD4+/CXCR4+) and HeLa Δ20 (Tat) cells transfected with the envelope of the pHXB2 clone of the HIV-1 IIIB strain (see table 2). The positive control with the wild envelope gives 1800 to 2000 foci. The negative control was made with an envelope of the MoMuLV retrovirus which does not produce any fusion foci under these conditions.
- no infection of lymphocyte cells activated with PHA (Phytohemaglutinine) and with interleukin 2 (IL-2) by viral pseudotypes obtained after complementing the genome of HXB2 ENV- (pNL4.3ΔENV) and the envelope (pHXB2 ENV) with W338S gp120, and the envelope inside 293T cells transfected with the 2 expression vectors. The positive control was formed of pNL4.3 ΔENV and pHXB2 ENV (wild type). The negative control was formed by a supernatant of the cells is transfected only with the expression vectors pHXB2 ENV.

STRUCTURE:

ELISA assay: Fixing of gp120 only to soluble CD4

FIGS. 4 to 8 give the results of the reactivity wild rgp120, gp120ΔaHX1 and gp120α3 W338S, with AcM CG10 (FIG. 4), AcM 4.8d(FIG. 6) and with Acm 17b (FIG. 8): in these assays, the rgp120s were deposited at a concentration of 1 μg/ml. The AcM was deposited at the concentrations shown on the abscissa. FIGS. 5 and 7 give the reactivity of these rgp120s complexed to CD4 with AcM CG10 (FIG. 5) and AcM 4.8d (FIG. 7) : In these assays the rgp120s were deposited at a concentration of 1 μg/ml. The CD4 concentration was 20 μq/ml and the AcM was deposited at the concentrations shown on the abscissa.

This mutation induces a trans-conformation which allows better exposure to the monoclonal antibodies 1.7b, 4.8d and G10 directed against the CD4i epitopes (induced CD4) (FIGS. 4, 5, 6, 7, and 8) which are epitopes that are unmasked after the fixing of gp120 to CD4. This transconformation was able to be detected in an ELISA system which was conducted as follows:

1. The bottom of the wells is coated with soluble CD4 (reference NIH) or with the antibody Aalto D7324 (which is s a goat antibody) directed against a linear peptide of the C-terminal region of gp120 (this antibody does not induce the trans-conformation to obtain unmasking of the CD4i epitopes).
2. After saturation with 3% BSA, gp120 is incubated with CD4 or with the antibody D7324 at 37° C. for 1 hour.
3. After 2 washings, one of the anti-CD4i AcM's (17b or 4.8d or CG10) is incubated with the previously attached gp120 (wild type or mutant) for 1 hour at 37° C.
4. The CD4i antibodies are developed with an anti-IgG antibody conjugated with peroxidase (POD).
5. The intensity of the reaction is read in the ELISA reader after halting the reaction.

The background noise shown by the controls (cells without gp120) is withdrawn from assay point results.

Remark: a control was made with gp120's detected by a rabbit polyclonal antibody directed against gp120 (FIG. 3).

These assays made with ELISA made it possible to verify that the anti-CD4i AcM's 17b and 4.8d indeed better recognize wild gp120 and muted gp120 when the latter are associated with soluble CD4, allowing unmasking of these epitopes. Although Acm CG10 does not at all recognize wild gp120 non-complexed to CD4, this AcM recognizes muted gp120 without it being complexed to CD4.

Interpretation:

The W338S mutation on gp120 induces the unmasking of the CD4i epitopes, in particular the epitopes recognized by AcM CG10.

This result is of importance since this mutation makes this mutant a good vaccine candidate exposing masked epitopes in infective viruses.

FACS Assay: Simultaneous fixing gp120 to at least 2 receptors present on the cell surface of the CEM lymphocyte line: CD4 and CXCR4.

In order to check that gp120 fix themselves to CD4 and CXCR4 respectively, the following assay was conducted: the CEM cells were firstly incubated with gp120, then incubated with monoclonal antibodies against the CD4 receptor (AcM OKT4a FITC supplied by ORTHO Diagnostic) and against the CXCR4 receptor (AcM 12GS supplied by Pharmingen) and then with appropriate mouse anti-1gG antibodies. .

Table 3 gives the average, fluorescence intensity of gp120 fixed to the CEM cells CD4+/CXCR4+ recognized by anti-CD4 Acm's.

TABLE 3

| Anti-CD4i AcM antibodies | AVERAGE FLUORESCENCE INTENSITY OF CP120 FIXED TO CEM CELLS CD4+/CXCR4+ | | |
|---|---|---|---|
| | without gp120 | wild gp120 | W338S gp120 |
| 4.8d | 5.65 | 76.775 | 208.76 |
| 17b | 5.21 | 70.48 | 175.575 |
| CG10 | 5.14 | 7.15 | 8.49 |

No labelling was observed which means that gp120 is effectively fixed to CD4 and to CXCR4.

The CEM cells cultured in RFMI 10% FCS were washed with a wash buffer PBS/0.3%/BSA/0.02% Na-azide (WB) and placed in an incubation buffer PBS/3%/BSA/0.02% Na-azide (IB) so as to place them in contact with wild and mutant gp120 for 1 hour at 37° C.

The cells were washed twice with the W8 then incubated in IB with one of the anti-CD4i antibodies (17b, 4.8d or CG10) at a concentration of 10 μg/ml for 1 hour at 25° C. The cells were then washed twice with WB, then incubated 45 minutes at 25° C. in IB with an appropriate anti-IgG antibody conjugated with. FITC or PE. After 3 washings with WB, the cells were replaced in suspension in IB and analysed under flow cytofluorometry (FACSort). 10,000 cells could be analysed one by one.

The results are given in FIG. 9. The 17b and 4.8d antibodies well recognize the muted gp120 but only scarcely recognize wild gp120. On the other hand, AcM CG10 no longer has access to its recognition site either on wild gp120 or on muted gp120.

Interpretation

If AcM CG10 no longer has access to its site but on the other hand AcM 17b and 4.8d do have access to this site, this means that the gp120 epitope strongly involved in the fixing of gp120 to the CXCR4 co-receptor is especially the one which is recognized by CG10.

Conclusion

W338S mutation on gp120 induces trans-conformation which prevents fusion and infection. This mutation prevents fusion when the envelope is expressed on the surface of transfected cells, and prevents infection when this envelope is positioned on the complemented virus. In addition, this trans-conformation allows unmasking of masked sites on wild gp120, due essentially to the fact that muted gp120 is recognized by AcM CG10 without this gp120 being complexed to CD4. The fact that this same AcM CG10 no longer has access to its epitope when this protein is associated with CD4 and CXCR4, and the fact that the anti-CD4i antibodies do not interfere with CD4, implies that it is the epitope recognized by AcM CG10 on gp120 which is involved in the fixing to CXCR4. Such mutant forms a candidate for conducting immunisations for the purpose of protecting against HIV infection.

BIBLIOGRAPHICAL REFERENCES

1. Kwong P. D., Wyatt R., Robinson J., Sweet R. W., Sodroski J. and Hendrickson W. A., 1998, Structure of an HIV gp120 envelope glycoprotein in complex with the CDM receptor and neutralizing antibody Nature, 393:648.
2. Missé D., Cerruti M., Schmidt I., Jansen A., Devauchelle G., Jansen F. and Véas B. 1998. Dissociation of the CDM and CXCR4 binding properties of human immunodeficiency virus type 1 gp120 by deletion of the first putative alpha-helical conserved structure. J. Virol 72:7280.
3. Cordonnier A., Montagnier L., and Emmerman M. 1989. Single amino-acid changes in HIV envelope affect viral tropism and receptor binding. Nature 340:571.
4. Hansen J. E., Lund O., Nielsen J. O., Brunak S. and Hansen J. E. S. 1996. Prediction of the secondary structure of HIV-1 gp120. Proteins 25:1.

What is claimed is:

1. An isolated and purified human immunodeficiency virus type 1 (HIV-1) mutant gp120 envelope glycoprotein comprising an amino acid mutation in position 112, consisting of replacement of W with S, I, or F, wherein said numbering scheme is based upon the molecular clone HxBc2.

2. The mutant of claim 1 further comprising at least one mutation of S at position 338 or position 427 for W or F at position 96 for W.

3. An isolated and purified human immunodeficiency virus type 1 (HIV-1) mutant gp120 envelope glycoprotein comprising an amino acid mutation in position 427 consisting of replacement of W with S wherein said numbering scheme is based upon the molecular clone HxBc2, or in position 338 consisting of replacement of W with S wherein said numbering scheme is based upon the molecular clone HxBc2.

* * * * *

SEQUENCE LISTING

```
<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: Description of artificial sequence:96W/S

<400> SEQUENCE: 1
aacgtgacag aaaatttaa catgagtaaa aatg                                34

<210> SEQ ID NO 2
<211> LENGTH: 27
<212> TYPE: DNA
<213> ORGANISM: Artificial Sequence
<220> FEATURE:
<223> OTHER INFORMATION: Description of artificial sequence:112 W/S

<400> SEQUENCE: 2
gatataatca gtttatctga tcaaagc                                       27

<210> SEQ ID NO 3
<211> LENGTH: 34
<212> TYPE: DNA
<213> ORGANISM: Artificial Sequence
<220> FEATURE:
<223> OTHER INFORMATION: Description of artificial sequence:96W/I

<400> SEQUENCE: 3
aacgtgacag aaaatttaa catgatcaaa aatg                                34

<210> SEQ ID NO 4
<211> LENGTH: 27
<212> TYPE: DNA
<213> ORGANISM: Artificial Sequence
<220> FEATURE:
<223> OTHER INFORMATION: Description of artificial sequence:112W/I
```

```
<400> SEQUENCE: 4
gatataatca gtttaatcga tcaaagc                                    27

<210> SEQ ID NO 5
<211> LENGTH: 34
<212> TYPE: DNA
<213> ORGANISM: Artificial Sequence
<220> FEATURE:
<223> OTHER INFORMATION: Description of artificial sequence:96W

<400> SEQUENCE: 5
aacgtgacag aaaattttaa catgtggaaa aatg                            34

<210> SEQ ID NO 6
<211> LENGTH: 27
<212> TYPE: DNA
<213> ORGANISM: Artificial Sequence
<220> FEATURE:
<223> OTHER INFORMATION: Description of artificial sequence:112W

<400> SEQUENCE: 6
gatataatca gtttatggga tcaaagc                                    27
```